United States Patent [19]

Osofsky

[11] Patent Number: 5,299,866
[45] Date of Patent: Apr. 5, 1994

[54] PEBBLE-BED HEATER AND SHOCK TUBE ASSEMBLY

[75] Inventor: Irving B. Osofsky, Rancho Palos Verdes, Calif.

[73] Assignee: Sparta, Inc., Torrance, Calif.

[21] Appl. No.: 918,585

[22] Filed: Jul. 22, 1992

Related U.S. Application Data

[62] Division of Ser. No. 552,862, Jul. 13, 1990, Pat. No. 5,197,323.

[51] Int. Cl.[5] .......................... B01F 5/06; B01F 15/06
[52] U.S. Cl. .................................... 366/336; 366/144; 366/146
[58] Field of Search ............... 366/336, 337, 338, 339, 366/340, 144, 145, 146, 147, 148, 149

[56] References Cited

U.S. PATENT DOCUMENTS

| | | | |
|---|---|---|---|
| 3,965,975 | 6/1976 | Edmundson | 366/336 |
| 4,204,775 | 5/1980 | Speer | 366/336 |
| 4,318,623 | 3/1982 | Curtis | 366/336 |
| 4,674,888 | 6/1987 | Carlson | 366/337 |
| 4,712,921 | 12/1987 | Sugiura | 366/336 |

Primary Examiner—Robert W. Jenkins
Attorney, Agent, or Firm—Beehler & Pavitt

[57] ABSTRACT

A shock tube assembly for simulating high energy detonations includes a driver section, a diaphragm section, an expansion nozzle, an expansion tube and an improved system for providing a heated and pressurized gas for the driver. After preheating the improved pebble-bed evaporator and superheater, gas or liquefied gas from a pressurized supply flows temperature. The output of the pebble-bedheater flows through a mixer for control of the temperature of the gas used to charge the driver. The pebble-bed heater is preferably vertically oriented and includes spaced baffles having flow apertures arranged in concentric circles. The apertures of each circle are connected by a groove to permit flow of gas through the aperture in the event that a pebble element rests on the open end of the aperture. This system allows very driver rapid fill times and makes possible the use of hot gas in uninsulated, unheated drivers to eliminate contact surface discontinuity and thereby produce near ideal static and dynamic pressure profiles.

2 Claims, 3 Drawing Sheets

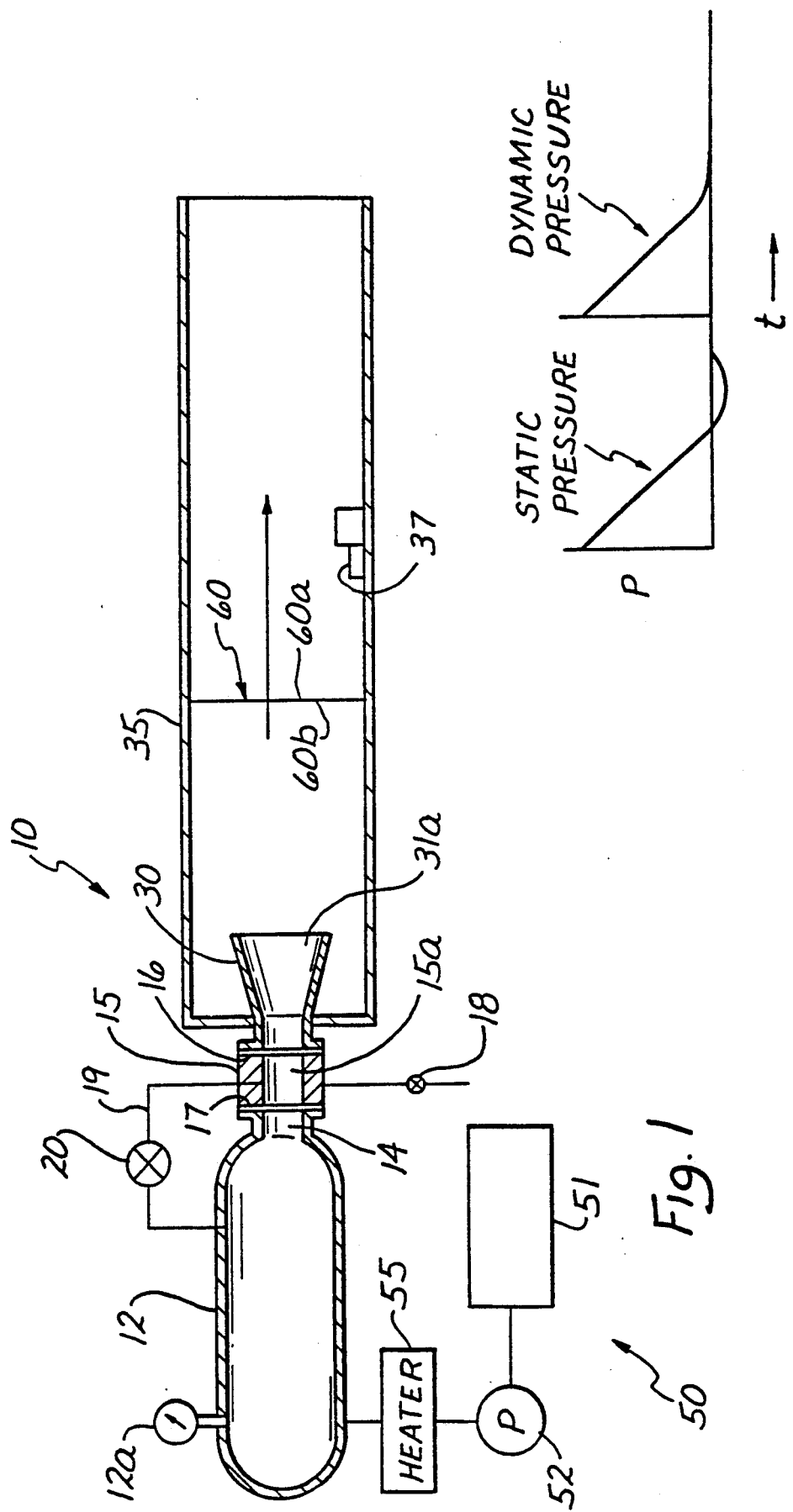

PEBBLE-BED HEATER AND SHOCK TUBE ASSEMBLY

"The Government has rights in this invention pursuant to Contract No. DAAA15-86-C-0115 awarded by the U.S. Army Armament Research and Development Command. The invention described herein may be manufactured, used and licensed by or for the Government for governmental purposes without the payment to us of any royalty thereon."

This is a divisional of copending application(s) Ser. No. 07/552,862 filed on Jul. 13, 1990, now U.S. Pat. No. 5,197,323.

FIELD OF INVENTION

This invention relates to pebble bed heaters and pebble bed heaters in combination with a shock tube assembly and more particularly to an improved pebble bed evaporator and super heater assembly, the latter especially adapted for, but not limited to, use with a shock tube assembly used to simulate the pressure and thermal conditions of a large energy blast, such as an explosive or nuclear blast, for example.

BACKGROUND OF THE INVENTION

It is known to use shock tube assemblies in order to simulate the static and dynamic pressure conditions resulting from large energy blasts. Radiant heaters such as oxygenaluminum powder rockets are used in the shock tubes to simulate nuclear blast temperature conditions on the target. These large energy blasts may be the result of conventional explosive detonation or nuclear detonation. By simulating the conditions of such blasts without an actual full scale detonation, it is possible to evaluate the effects of such blasts on various types of equipment ranging from relatively small test articles such radios and the like, to relatively large test articles such as full size operational shelters, vehicles, tanks and aircraft. In effect, the shock tube assembly is a specialized short duration wind tunnel used for test and evaluation of various structures.

Typically, a shock tube assembly includes various sections, such as a driver section containing the pressurized gas which is ultimately used to create the shock wave, a diaphragm section to suddenly release the driver gas, an expansion nozzle section to port the driver gas into an expansion tube, along with associated gas processing and support equipment. The test article to be tested is placed in the test section of the expansion tube.

The driver is normally a hollow cylindrical pressure vessel with one end closed and sealed at the other end by the diaphragm section and capable of holding room temperature or elevated temperature gas at substantial pressure. The diaphragm section, associated with the driver, includes one or more diaphragms which are ruptured to release the gas in the driver, i.e., the shock tube diaphragm is mechanically, explosively or pressure ruptured to suddenly release the gas from the driver. In a dual diaphragm system, only one diaphragm is ruptured and the higher pressure differential imposed on the second diaphragm bursts it to release the gas. From the diaphragm section, the gas flows through the expander nozzle section, the discharge end of which is located within the expansion tube. The gas flowing through the nozzle section is supersonically expanded within the expansion chamber to create a shock wave which travels down the elongated expansion tube, compressing the air behind the travelling shock wave interface thereby providing both the static and dynamic pressure conditions and temperature conditions for testing and evaluating the test article located within the expansion tube and which is exposed to the static and dynamic pressure generated by the shockwave. Normally, one test article is tested in each firing and the test article usually is not larger than 10% of the cross-section of the expansion tube.

Shock tube assemblies may be of various sizes depending upon the blast conditions to be simulated and the test articles to be tested. For example, one such assembly for generating overpressures of about 200 psi, includes a driver section about 40 cm in length with an expansion tube having a length of about 100 cm and a diameter of about 7.5 cm. Such a system may use helium gas as the driver gas, the latter pressurized to about 1,345 psig at a temperature of 530 degrees R to generate a shock wave travelling at Mach number=3.5 with a 200 psi static overpressure in the expansion tube. Other shock tube systems may include one or more drivers of roughly 2 meters in diameter and having a length of from 43 to 93 meters. The expansion tube may be semicircular having a diameter of 20 meters and a length of between 200 to over 300 meters. These larger systems are capable of generating the desired static overpressures of about 35 psi and shock waves which travel at supersonic speed in the expansion tube with driver pressures of 2,250 psig.

It is recognized that there is a well known relation between the driver pressure ratio (ratio of driver pressure to ambient pressure) required to produce a shock wave of a given shock pressure ratio (ratio of the pressure behind the shock wave and ambient pressure) for a given expansion ratio (ratio of nozzle area to expansion tube area). Thus, the pressure of the gas in the driver effectively controls the shock pressure ratio. A second factor is the temperature of the gas in the driver. Upon release and flow of the gas through the expander nozzle, a contact surface is formed between the generated and moving shock wave and the air in front of the shock wave. It is important that the gas static temperature on each side of the contact surface be the same, i.e., no contact surface temperature discontinuity. This simulates the real world in which an explosion induced shock wave races through the ambient temperature air to impinge on the target. Air on both sides of the shockwave is initially at the same temperature. Gas at rest has only one temperature which is called total temperature. The total temperature is a measurement of the energy in the gas at a given pressure. When some of the internal energy of the gas is used to accelerate the gas to a velocity, the total temperature of the gas remains constant and a stationary thermometer inserted into the flow would measure the initial total temperature. However, if a thermometer could be inserted into the gas stream so that it moved with the stream at the stream velocity, it would measure the static temperature which is lower than the total temperature. The relationship between total temperature and static temperature is defined by the following equation:

$$T_o = T_s * (1 + (k-1)/2) * M^2)$$

where:
$T_o$ = Total temperature, degrees R
$T_s$ = Static temperature, degrees R k = ratio of specific heats = $C_p/C_v$ = 1.4 for air
M = Mach number
For M = 2.66, $T_o/T_s$ = 2 and for the static temperature at both sides of the shock in the expansion tunnel to be equal, the driver gas must be heated to 1,040 degrees R if ambient temperature is 520 degrees R (60 degrees F.). If the temperature of the gas on the expander side of the contact surface is higher than that on the other side, then the generated dynamic pressure will be lower than desired. If the temperature of the gas on the expander side of the contact surface is lower than that on the other side, then the dynamic pressure will be higher than desired. In either case, the test does not accurately simulate the blast conditions.

The temperature of the gas in the driver may be calculated such that on expansion, the temperature of the expanded gas is equal to that on the other side of the contact surface. Elimination of contact surface temperature discontinuity may be achieved by control of the temperature of the gas in the driver according the relationship in the example equation. Thus, it may be necessary, for example, to maintain the temperature of the gas in the driver as high as 700 degrees F.

The following table indicates some of these typical and representative relations calculated on the basis of a 600 kiloton nuclear detonation:

| Shock Overpressure psig | Driver Overpressure psia | Driver Temperature Degrees R |
| --- | --- | --- |
| 35 | 1727 | 1137 |
| 30 | 1507 | 1037 |
| 25 | 1249 | 947 |
| 20 | 1017 | 857 |
| 15 | 785 | 763 |
| 10 | 309 | 671 |
| 5 | 279 | 570 |
| 2 | 99 | 534 |

It is therefore apparent that the design of the gas supply system is not separable from the design of the driver because of the dynamic coupling between the two when they are used together in the compression/heating cycle of shock tube operation.

Given the need to maintain the gas in the driver at an elevated temperature for proper dynamic pressure simulation, formidable practical, economical and structural problems are presented. For example, the use of external heater coils surrounding the driver unit is economically prohibitive because of the size of the driver unit and the power costs to heat such external units and because of the time required to change from one temperature to another for various test conditions. Even for smaller driver units, the power costs are impressively high relative to the physical size of the driver. The use of internal insulation to maintain the temperature of heated gas within an unheated driver is fraught with problems, not the least of which is the need for an insulating material which can be reliably fastened to the driver wall, which insulator is non-porous, and is capable of withstanding temperatures of the order of 700 degrees F. or more, as will be apparent from the following discussion. Such an insulation and attachment mechanism has not been found after lengthy investigation.

In shock tube assembly operation, the typical sequence is to initially charge the driver with a pressurized gas at the proper predetermined pressure and temperature level. Once fired, the internal pressure and temperature within the driver drops rapidly to atmospheric pressure and in some cases drops to a negative pressure. If an insulation is used which is porous, i.e., has pinholes, the initial pressurization causes the gas to travel through the pinhole to the interface between the driver internal wall and the insulation. Upon firing, the sudden drop in pressure causes the pressure at the interface to blow the insulation inwardly and generally results in total effective loss of the insulation. Thus, the driver must be re-insulated between each firing, an operation which is quite expensive. Tests have shown that if the insulation is porous as in conventional firebrick, the gas under pressure permeates the ceramic and causes it to literally explode when the driver pressure suddenly drops.

Even if the insulation is pinhole free and capable of withstanding relatively high temperatures, there is the problem of differential expansion between the metal wall of the driver and the insulation. Effectively what occurs is that at room temperature the insulation may be bonded to the metal wall. The heavy driver wall expands due to the internal pressure at a greater rate than the insulation and bond, causing the insulation to part from the wall. Normally, the gas in the driver is rapidly discharged upon firing and the pressure within the driver may drop to minus 10 psig in one second. This sudden drop in pressure causes the unbonded insulation to part from the driver wall. Once the insulation has parted it is removed from the wall by pressure, gravity or aerodynamic forces and therefore is ineffective for later shots.

One possible alternative is to use a double lined driver in which the insulation is placed between the heavy outer metallic wall and a thin inner metallic wall. Typically such an insulation may be fire brick. Here, the problem is one of economics due to the relatively high cost of installing the fire brick, the cost of the inner wall and the additional cost of the larger, thicker outerwall. Another approach is to circulate the gas in the driver through an external heater assembly Due to the high pressure, high density and high temperature of the gas within the driver, this alternative requires blowers which can produce mass flow rates necessary at the high temperatures and pressures. Such equipment is not commercially available and would be extremely costly to design and build.

Among the other problems is that of initially charging the driver with gas at the proper pressure and temperature. As a practical matter, the time needed to charge the driver cannot be too long. For a 20 meter diameter shock tube calculated charge times of 16 hours are not acceptable with uninsulated drivers and this is about the length of time it would take with large air compressors filling a building 150 feet square. Such a system suffers from the disadvantage of large pressure drops in the tube type external heater and an air compression system which would charge the driver in 15 minutes or less would be prohibitively costly. The 15 minute charging period had been calculated as the maximum charging time that could be used to fill an unheated driver with heated pressurized gas; however, recent calculations show that the charging time should probably be reduced to 5 minutes or less.

It is thus apparent that advantages exist in providing a driver capable of containing a gas at a relatively high pressure and temperature and which is capable of being charged very quickly with a heated and pressurized gas to be used in the shot.

It is also apparent, due to the relation between the temperature of the gas on one side of the contact surface and on the other side thereof, that a need exists for a gas charging system which accurately controls the temperature of the gas charging the driver while providing the proper pressure in a time sufficiently short to allow operation of the shock tube before heat transfer from the hot gas to the uninsulated driver wall cools the gas below the required temperature.

It is also desirable to provide a superheater and evaporator capable of rapidly heating a gas or liquified gas to an elevated temperature and in which the temperature of the output gas may be easily controlled, especially at high volumetric delivery rates.

It is also well known from simple thermodynamic relationships that it takes much more power to compress a weight of gas to an elevated pressure than it takes to pump a relatively incompressible liquid to that pressure and evaporate the liquid to gas at the elevated pressure. That is the way steam engines work and the boiler feed pump takes a relatively minuscule amount of power to supply pressurized water to a boiler which evaporates the water to steam which runs the steam engine that powers the pump and yields a net output. Similarly, it takes only a fraction of the power required by air compressors for piston type cryogenic pumps to raise the pressure of cryogenic liquid nitrogen to 2,250 psig and to pump it through a pebble-bed heater which evaporates it to produce hot gas at the required temperature.

It is also apparent that the provision of a gas charging system, in the form of an improved and effective pebble-bed heater, for a shock tube assembly which is relatively inexpensive and reliable offers unique advantages.

BRIEF DESCRIPTION OF THE INVENTION

By the present invention, a shock tube assembly is provided in which the gas used in the shot may be provided rapidly, at the proper pressure and temperature thus reducing the cycle time between shots, i.e., the time interval between the start of charging of the driver to the shot time and reducing the degree of superheat required for the driver gas.

This is accomplished in accordance with the present invention by the use of a unique pebble-bed evaporator and superheater assembly, capable of uses other than with shock tube assemblies, and which capable of providing large volumes of pressurized gas heated to a controlled temperature in a relatively short period of time with a pressurization power requirement that is a mere fraction of the power required by mechanical gas compressors.

Due to the need for relatively accurate control of the temperature of the heated and pressurized gas, one aspect of this invention relates to the relatively simple and effective mechanism by which the gas is heated and by which the temperature of the gas is controlled just prior to introduction into the driver or other device for which the gas is intended.

In brief, the shock tube assembly may be of any of the designs which are themselves well known and which have been described. The gas supply system includes a gas storage system for gaseous or liquified gas such as nitrogen, helium or any other inert gas. Gas or liquified gas from the storage system flows through a compressor or pump (for the liquid) and then to the evaporator/superheater unit and then to the driver. The evaporator/superheater is a single pass pebble-bed superheater, appropriately baffled in a unique manner to assure proper and uniform flow of gas through the pebble-bed for proper and uniform heating thereof in a relatively short time period. Connected to the output of the evaporator/superheater is a mixer section whose function is to assure that the temperature of the pressurized and heated gas is uniformly within predetermined limits prior to flow to the driver to charge the same. Typically, the mixer functions to reduce the temperature of the pressurized gas exiting the heater prior to flow into the driver. Due to possible heat losses through the driver wall, the gas is normally heated in the pebble-bed heater to a superheat temperature above that needed in the driver. Further, the temperature of the gas exiting the pebble-bed heater may vary over time, i.e., it is hotter at the start of a charging operation than towards the end of that operation. The mixer section in accordance with this invention, mixes two right angle streams, one of which is hot gas exiting from the pebble-bed heater and the other is a stream of cryogenic nitrogen or a stream of room temperature gas. It is difficult to mix the streams of gas uniformly in a small chamber. Thus, in accordance with this invention the combined stream of partially mixed gas is forced to flow through a small pebble-bed which has sufficient heat transfer capability to make the exiting mixed stream uniform in temperature. This is a very important feature of the mixer because it reduces the mixer volume and complexity, which in turn reduces cost of fabrication.

In a typical sequence, the evaporator/superheater is purged and heated to the desired temperature. Heating may be by gas burner or internal electric cartridge heaters to bring the pebble-bed to the desired temperature. Once preheated, the gas burner or cartridge heaters are turned off and the superheater evaporator operates as a heat storage device for single pass heat transfer, at relatively high volumetric flow rates, to an input gas or liquified gas. The result is an output of gas at the desired temperature and at relatively high volumetric rates.

Depending on the nature of the source gas fluid, gas or liquid, the pebble-bed heater may act both as an evaporator to convert the liquid to a gas and heat it, or it may act primarily as a superheater to heat the inlet product in gaseous form. The result is that the output gas of the pebble-bed heater is normally at a higher temperature than needed for effective driver operation and shock wave production free of contact surface temperature discontinuities. However, it is important that the temperature of the gas in the driver, at the time of firing, be closely controlled and that thermal loss through the driver wall be taken into account in the superheat temperature of the initially charging gas.

By the present invention, the control of the temperature of the infeed gas to the driver is controlled by a mixer unit which monitors the temperature of the pressurized gas exiting the mixer unit and adds cooling gas, in liquid or gaseous form, to reduce the temperature of the mixed output to the desired temperature. That output of the mixer is thus of the correct predetermined temperature, account having been taken for thermal loss through the driver wall. Accordingly, at the time of firing, the gas in the driver is at the proper temperature and pressure to create the proper replicate of the dynamic and static pressure and temperature conditions for the intended blast-detonation conditions.

Another aspect of the present invention is the design of the pebble-bed heater itself. Because the preferred form of the pebble-bed heater is a vertical arrangement, in order to achieve gravity packing of the pebbles with resultant uniform flow of the gas through the heater, the baffles are apertured for flow from one section to another. One problem is that in such an arrangement, one or more spherical pebbles may rest over the aperture of the baffles thereby preventing uniform flow through the assembly. To overcome this potential problem, grooves are provided which interconnect at least some of the apertures of each baffle such that if a pebble rests on the open end of any aperture, gas may flow for the groove to the aperture to the next section without obstruction.

Another feature of the pebble-bed is that the heated pebbles and baffle plates are confined within a stainless steel, heat resisting or superalloy cylinder which also reaches the pebble temperature which can be on the order of 1,800 degrees F. These materials are very expensive so to minimize costs, the pressure shell was insulated from the heated pebble assembly and is constructed from conventional ASME Boiler Code material suitable for low temperatures. The mixer is also insulated but because parts of are in contact with cryogenic liquid, it was made from stainless steel.

It will thus be apparent from the following detailed description that various forms of the present invention may be practiced. The following description is intended for purposes of illustration only and is not intended to be a limitation on the present invention.

DETAILED DESCRIPTION OF THE DRAWINGS

FIG. 1 is diagrammatic illustration of a shock tube assembly for purposes of understanding of this invention;

FIG. 2 is a diagrammatic illustration of the static and dynamic pressure conditions created by the shock wave;

DETAILED DESCRIPTION OF THE INVENTION

Figure 3:
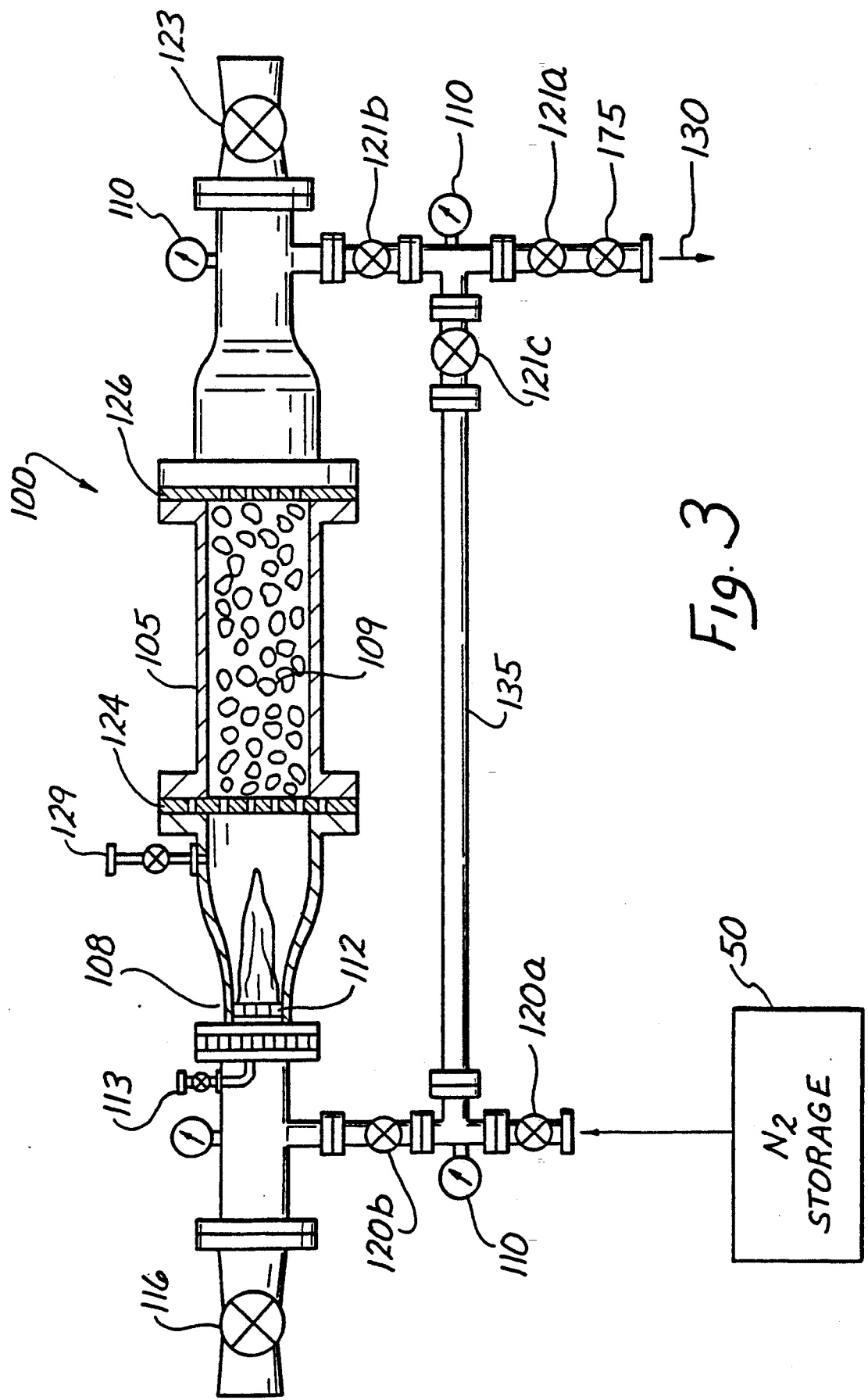
FIG. 3 is a diagrammatic illustration of the evaporator/superheater pebble-bed heater in accordance with this invention.

Referring to the drawings which illustrate a preferred form of the present invention, FIG. 1 is a diagrammatic illustration of a shock tube assembly 10 in accordance with this invention. The assembly generally includes one or more driver units 12, with a pressure gage 12a, the drivers containing a gas at a predetermined temperature and pressure as may be needed to generate the shockwave. In the form illustrated, the driver may be a generally cylindrical container containing a gas such as air or nitrogen gas although other inert and non-toxic gases may be used. As seen, the one end of the driver is open as at 14 but is sealed by a diaphragm assembly 15.

The diaphragm assembly may include one or more diaphragms 16 and 17, spaced from each other, to form a chamber 15a therebetween. A vent valve 18 may be connected to the chamber 15a while a pressure by-pass line 19 and pressure regulating valve 20 interconnects the driver and the chamber 15a to pressurize the chamber at approximately 50% of the driver pressure. Because the driver is pressurized to a relatively high pressure with a heated gas, e.g., 2,250 psi at 700 degrees F., for example, the diaphragm 17 normally would have to be rather thick to withstand such pressure. When the diaphragm bursts, the petals formed must bend a full 90 degrees to fully open and the amount of metal strain at the bend of a thick plate will probably exceed the allowable, causing cracks and rupture at the bend line. Thus, when fired, it is possible that fragments of the thick diaphragm may be propelled supersonically down the shocktube. To reduce the tendency of such high velocity relatively large projectiles from the fragmented diaphragm, the by-pass system operates to provide a pressure approximately 50% of the driver pressure on the back side of diaphragm 17 thereby reducing the thickness needed for the diaphragm and reducing the fragment size. This requires a second diaphragm 16 of equal thickness. Another reason that thin diaphragms are advantageous is that the thick petals formed when a single high pressure diaphragm is burst, may not fully open to allow full flow of the gas. Furthermore, dual diaphragms can be actuated without the use of explosives by venting chamber 15a with valve 18. When the chamber pressure drops to approximately 25% of driver pressure, the upstream diaphragm 17, ruptures and the gas pressure rise in the venting pressure ruptures downstream diaphragm 16. Some operators merely increase the pressure in chamber 15a until diaphragm 16 ruptures, followed by diaphragm 17. Both methods have advantages and disadvantages.

Connected to receive the gas from the diaphragm section 15 is a supersonic expansion nozzle 30. The nozzle may be any one of several different types such as a diverging nozzle or a converging-diverging nozzle (DeLaval). A DeLaval nozzle operates quite satisfactorily. The open end 31a of the nozzle is located in an expansion tube 35, the latter in the form of elongated tube which may be semi-circular, rectangular or cylindrical, depending upon design. Located within the expansion tube 35 is the test article 37 to be tested. The expansion tube may be of the open or closed type, that is, the end of the tube near the expansion nozzle may be sealed to the outer surface of the nozzle or the end of the tube may be open.

Also forming part of the shock tube assembly is a gas supply system generally designated 50 and may include a supply 51 of the gas to be used, either as a pressurized gas or a liquified gas, although cryogenic liquid nitrogen gas is preferred in accordance with this invention. Gas from the storage system is flowed through a pump 52 and then to the pebble-bed evaporator/superheater 55 in accordance with this invention. The output of the pebble-bed evaporator/superheater is connected to the driver 12, as illustrated.

In a typical sequence, the test article 37 is placed in the expansion tube 35 and the instrumentation on the test article is prepared to measure and record data. Valve 18 is closed while valve 20 is opened to the proper setting to bleed off the desired pressure from the driver 12 into chamber 15a. Gas from the supply system 50 is then heated to the proper superheat temperature in the pebble-bed heater 55 and used to pressurize the driver with superheated pressurized gas. When the driver is charged and the superheat temperature drops to the operating temperature, valve 20 is closed and vent valve 18 is opened. As pressure in chamber 15a drops, upstream diaphragm 17 ruptures followed by rupture of the second downstream diaphragm 16. Heated pressurized gas then flows through the nozzle 30 where it is supersonically expanded to create a shock wave generally indicated at 60 and which travels down the expansion tube, as indicated by the arrow, compressing the gas on the aft side 60b of the shockwave to create the desired overpressure conditions. The gas on the front side of the shock wave 60c is undisturbed until the shockwave reaches it.

As noted, static overpressures may be in the range described earlier. The total elapsed time for the actual test, from firing to dissipation of the shock wave, is quite short As earlier noted, in order to replicate blast conditions it is necessary that the static pressure and dynamic pressure conditions be controlled. Referring to FIG. 2, the plots of static and dynamic pressure conditions are illustrated. As seen, the static pressure increases quite rapidly and over a short period of time is reduced to atmospheric and may even fall below atmospheric pressure. The dynamic pressure curve follows that of the static pressure curve but without the negative pressure component, each of these plots representing the pressure conditions at the target or test subject.

To achieve the proper pressure conditions, there should be no contact surface discontinuity, i.e., the static temperature of the gas on side 60a should be the same as the static temperature of the gas on side 60b of the contact surface, illustrated as 60. This replicates what happens when a blast wave travels through ambient air towards a target. To achieve this control of the gas static temperature, the temperature of the gas in the driver must be controlled, having in mind that there are heat losses through the driver wall and cooling of the gas during expansion.

Referring to FIG. 3, the diagrammatic arrangement of the pebble-bed heater and gas supply assembly 100 is illustrated. In the form illustrated, the pebble-bed heater 105 is heated by a fuel fired burner unit 108, although other heater systems may be used such as electrical resistance heater elements such as "Calrods". The pebble-bed material may be nickel-iron alloy (Ni-Resist) or ceramic (Alumina) spheres ⅜ of an inch in diameter for example, as indicated at 109. Actually, smaller diameters may be advantageous and larger diameters have less heating area. In this form, the gas to be heated and pressurized is cryogenic liquified nitrogen gas provided from a gas supply system 50. The system is instrumented with pressure gages 110 and various valves, and thermocouples for measurement of temperature.

Fuel for the burner 112 is supplied by a fuel inlet 113 and valve 116 is opened for flow of air to the burner 112. Valves 120a and 120b are closed as are valves 121a, 121b, and 121c. Flow shutoff valve 123 is opened and the burner is fired to heat the pebble-bed contained between spaced perforated ceramic or superalloy plate 124 and perforated steel or superalloy plate 126. A compressed air inlet 129 may be used to control the temperature of the pebble-bed during the preheating operation by mixing cold excess air with the hot combustion gases.

Burner exhaust may be vented to atmosphere or directed to the driver to preheat the latter and the fill pipe. The preheating of the pebble bed heater continues until the latter reaches the proper predetermined temperature, which takes about one hour, for example. Thus heated, the pebble-bed acts as a stored heat source for the gas. Once proper pebble-bed temperature is reached, valves 116 and 123 are closed and the burner is shut off.

The next phase is the gas heating phase. Valves 120a and 120b as well as valves 121a, 121b and 121c are opened. Pressurized gas from the gas supply 50 flows through valves 120a and 120b into and through the heater 105, in a single pass, where the gas temperature is increased substantially to pebble-bed temperature by the time that it exits through plate 126. If cryogenic liquid nitrogen issued, it flows from liquid nitrogen gas supply 50 through valves 120a and 120b into heater 105. It strikes the hot pebbles after passing through plate 124 and flashes from liquid to gas in the first part of the pebble-bed and is heated substantially to pebble-bed temperature by the time that it exits through plate 126. The heated gas exits through valve 121b and 121a to the outlet 130 for the heated gas, the latter connected to the gas input of the driver 12. The temperature of the heated output gas is monitored by a thermocouple 175 relative to the desired temperature in the driver.

One aspect of this invention is the provision of a mixer unit to control the temperature of the gas leaving the pebble-bed heater prior to flow into the driver. Interconnecting the cold side of the gas infeed section and the heated output of the pebble-bedheater is a bypass line 135 with the flow through the bypass line being controlled by valve 121c. Control of the temperature of the gas exiting from outlet 130 is provided by the valve 121c which bleeds room temperature gas or cryogenic liquid gas which is mixed with the superheated gas exiting the pebble-bed heater. Valve 121c is a throttle valve which is controlled in accordance with the temperature of the gas charging the driver. If the input to the driver is too hot, it is cooled by mixing room temperature gas or cryogenic liquid gas with the superheated output of the pebble-bedheater. Valve 121c may be manually or automatically operated. Once the driver is charged with pressurized gas at a predetermined temperature, normally less than the temperature of the output as measured at valve 121b, all the valves are shut off and the driver charging sequence is completed unless a flow is desired to top off the driver as it loses temperature or is vented.

It is known, for example, that there is a heat loss through the wall of the driver even if insulated. Heat loss to the driver wall is a maximum when the differential temperature between the gas and the wall is the greatest. For example, for a driver wall temperature of 290 degrees K., in five minutes the gas temperature will drop from 700 degrees K to about 649 degrees K. In ten minutes the gas temperature drops to about 605 degrees K. These losses are taken into account during the operation of the pebble-bed heater and mixer in order to provide gas in the driver at the proper temperature and pressure for the shot. Thus, to reduce excessive heat loss, driver charging time should be very short. That is accomplished by the present invention which has extremely high heat transfer rates and low pressure drop.

In the event that the temperature of the gas in the driver is too hot, the driver walls will cool the gas in a matter of minutes. Another factor is that a significant amount of energy remains stored in the pebble-bed heater even after charging. Accordingly, the stored heat can be used to supply additional heated gas during any firing hold period.

Figure 4:
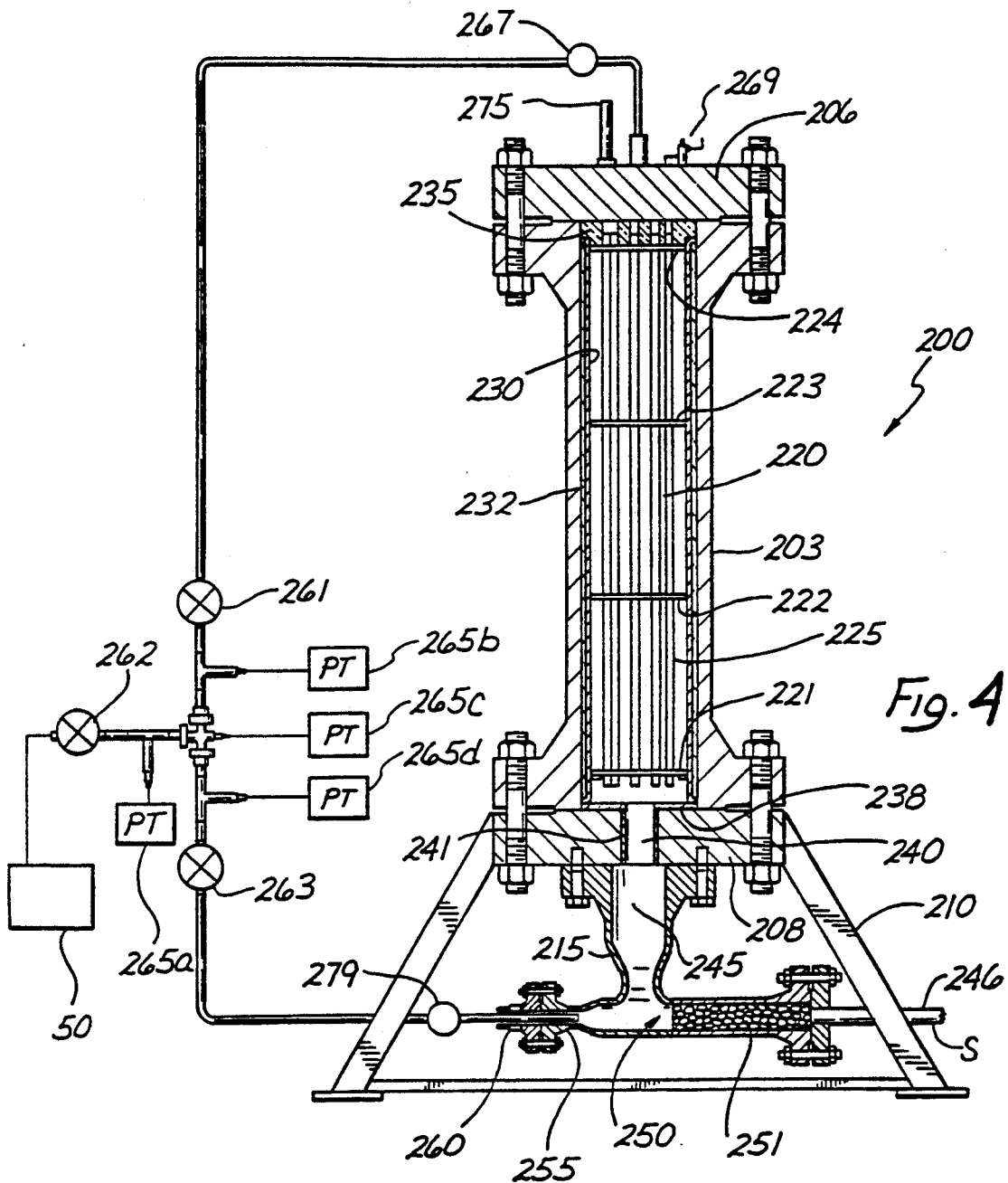
FIG. 4 is a view, partly in section and partly in elevation, of the evaporator/superheater pebble-bed heater in accordance with this invention.

FIG. 4 illustrates the details of a preferred form of pebble-bed evaporator/superheater assembly 200 in accordance with this invention. While the pebble-bed unit 200 has been described as having unique advantages when used to charge the driver of a shock tube assembly, it will be appreciated that the assembly may be used with other types of equipment and still provide the advantages of effective heat transfer to pressurize and heat a gas to a desired and controlled temperature. If cryogenic liquid gas is used as a gas source, a simple piston type or centrifugal pump can supply the flow at desired pressure with high efficiency and minimal work because the liquid is almost incompressible. Flow rate is governed primarily by pump size and horsepower. The use of electrical resistance heater elements also permits continuous operation of the unit, if desired, but the power output of the electric heaters is negligible when compared with the power output of the pebble-bed heater.

The unit 200 includes an outer generally cylindrical shell 203 of carbon steel, for example. The shell is open at each end and closed at the top by an inlet header 206 which is bolted to the upper end of the shell, as shown, and closed at the bottom by an outlet header 208 bolted to the lower end of the shell, as shown. Affixed to the outlet header is a frame assembly 210 such that the unit 200 is supported in a generally vertical orientation. Bolted to the outlet header is a mixer assembly 215 arranged generally horizontally and whose function has been briefly described.

Located within the shell 203 is a heater and baffle assembly 220 comprised of spaced baffle plates 221, 222, 223 and 224 which are apertured for flow of gas through the plates and which are apertured to support heater tubes 225 which pass through the plates and form a passage for the electrical resistance heater elements 275. There may be 9 or more tubes for nine or more heater elements which extend from the top of the shell to the lower baffle plate 221, the upper end of each of the tubes being secured to the inlet header with a gas tight joint. The ends of the heater elements 275 extend above the inlet header as shown. Thus, if there is a problem with any heater element, it may be withdrawn from the tube and a new heater element inserted without the need to disassemble the pebble-bed heater structure.

The heater and baffle assembly 220 also includes a metallic cylindrical housing shell 230 spaced from the inner wall of the outer shell 203. In the space between the shells, there is located an insulator 232 which may be a woven ceramic fiber blanket. The upper end of the shell 230 is spaced from the underside of the inlet header 206 with a ceramic fiber insulator 235 located in the space, the insulator being apertured for passage of the heater support tubes 225 therethrough. The lower end of shell 230 is spaced from the upper surface of the outlet header 208, a high density alumina insulator 238 being located in the space. As shown, the outlet header is provided with a passageway 210, the latter lined with an alumina silica insulator 241. Passageway 240 communicates with the superheated gas inlet 245 of the mixer section 215. The volume of the shell 230 from the upper baffle 224 to the lower baffle 221 is filled with substantially spherical pebbles of the type described.

The outlet 246 of the mixer 215 is downstream of a pebble-bed mixing chamber 250, the latter including a pebble-bed section 251 being located between the outlet 246 and the superheated gas inlet 245. Mixer section 215 and other internal portions of the mixer may be insulated to conserve stored heat, if desired. The spheres in the pebble-bed section 251 may be of the same materials previously described but may be smaller in diameter, e.g., about 0.5 of an inch in diameter, for example. The mixing chamber includes a second inlet 255 from a source of low temperature gas or liquified gas which flows through a nozzle 260 into the mixing chamber. During the preheat phase, only the pebbles in the pebble-bed shell 230 are pre heated. If desired, the mixer and its pebble-bed could be pre-heated.

Gas or cryogenic liquified gas from a storage supply 50 and pump flows through a feed system which includes valves 261, 262, and 263, each of which may be a cryogenic valve. The portion of the feed system between these valves is provided with a plurality of pressure transducers 265a, 265b, 265c and 265d for monitoring the pressure at the point indicated. The portion of the feed system between valve 261 and inlet header 206 includes a one way check valve 267 permitting flow to the pebble-bed heater but not in the reverse direction. The inlet header also includes a pressure relief valve 269. A second one way check valve 279 is located downstream of valve 263 and upstream of nozzle 260 to prevent flow of gas towards valve 263. The infeed header also includes a nozzle arrangement for flow of gas or liquified gas into the pebble-bed heater.

As noted, the shell is oriented in a vertical position such that the surfaces of the respective baffles are in a spaced horizontal orientation. The heater rod tubes assist in maintaining this orientation. The spherical pebbles essentially occupy the volume between adjacent baffle elements and thus, gravity maintains the spheres located above each baffle element in contact with the underlying baffle, the latter apertured to permit flow of the gas around the open spaces between the spheres and through one baffled section to that beneath it. One problem which such an efficient arrangement presents is that one or more of the spheres may land on the open end of one or more of the flow apertures in the baffles thereby obstructing flow of the gas through the shell For effective and efficient heat transfer from the spheres to the gas and for overall efficient heat transfer, it is desirable that the flow and the transit time through the pebble-bed heater be uniform, with no hot spots forming.

Figure 5:
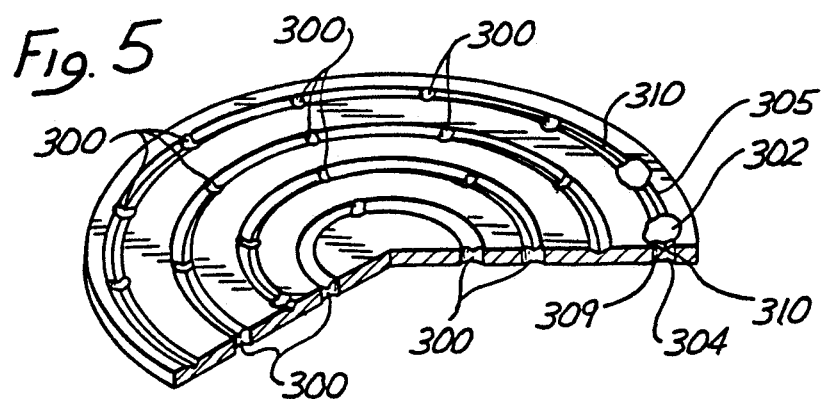
FIG. 5 is a fragmentary view, partly in section and partly in elevation, of one of the baffles of the pebble-bed heater in accordance with this invention, for purposes of explanation.

Referring to FIG. 5, a fragmentary section of one baffle is illustrated and includes a plurality of gas passages 300 therethrough, as contrasted to the heater tube apertures. The gas passages may be on the order of 0.25 of an inch in diameter, which is smaller than the diameter of the spheres, and are arranged in symmetrical concentric circles for uniform flow of the heated gas through the shell of the pebble-bed heater. The gas passages may be arranged in other geometrical patterns such as a rectangular grid pattern of spaced parallel lines or other pattern to provide uniform flow. Since the spheres are held down on the baffle plate surface by gravity, it is possible that a particular sphere, for example 302 may come to rest over a particular gas passage, for example 304. Because the sphere diameter is greater than the diameter of the gas passage, the sphere would tend to block the passage and inhibit flow of gas through that passage. To prevent obstruction of any gas passage, the gas passages of each circular track or the track of other geometric patterns are interconnected with a groove 305, illustrated as being generally V-shaped.

Preferably, the width of the groove is approximately the same as the diameter of the gas passage and of a depth which leaves an open space 309 beneath the lower surface of the sphere and the base 310 of the groove. In this way, even if a particular gas passage is occupied by a sphere, gas may flow along the surface of the baffle and in the groove 305 and through the open space into the gas passage thereby assuring virtually unobstructed flow of gas through the pebble-bed heater.

In operation, the pebble-bed heater is preheated absent the flow of gas or liquified gas, to the desired temperature as already described. Thereafter, gas flow is commenced and in a single pass through the pebble-bed heater, the gas temperature is elevated to a first superelevated temperature above that desired. The temperature of the superheated gas exiting though output 246 is monitored sand valve 263 is opened to permit flow of cooling gas or cryogenic liquified gas through the nozzle 260 into the mixing chamber 250, through the pebble-bed mixer and to the output 246 and then to the targeted destination.

It is thus apparent that the pebble-bed evaporator and superheater of the present invention provides unique performance, especially in connection with shock tube assemblies. It will be apparent that various modifications may be made by those skilled in the art based on the detailed description herein which modifications are deemed to come with the scope of the present invention as set forth in the appended claims.

What is claimed is:

1. A mixer device for mixing a cryogenic gas with a heated gas for producing an output mixed gas stream having a predetermined temperature which is greater than the temperature of said cryogenic gas and less than the temperature of said heated gas, comprising:
    a mixing chamber,
    inlet means in said mixing chamber for receiving the cryogenic gas,
    second inlet means in said mixing chamber for receiving said heated gas,
    said mixing chamber having an outlet through which said mixed gases exit,
    means to monitor the temperature of the mixed gases exiting the mixing chamber, and
    means to control and vary the flow of the cryogenic gas into said mixing chamber whereby two flowing streams of gas are converged and mixed, with each stream being at a different temperature and the combined stream exiting the mixing chamber is at a uniform temperature that is at a level between the temperatures of the incoming gas streams.

2. A mixer device as set forth in claim 1 wherein said mixing chamber includes a pebble-bed mixer section through which the said mixed gas streams are forced to flow through the pebble-bed mixer section to increase the mixing and increase the uniformity of the tempera of the combined gas streams.

* * * * *